(12) United States Patent
Li et al.

(10) Patent No.: US 12,385,810 B2
(45) Date of Patent: Aug. 12, 2025

(54) DEVICE FOR IN-SITU MEASUREMENT OF SUBSTANCE MIGRATION AND TRANSFORMATION ON SEDIMENT-WATER INTERFACE

(71) Applicant: South China Institute of Environmental Science, MEE (Ecological and Environmental Emergency Research Institute, MEE), Guangzhou (CN)

(72) Inventors: Weijie Li, Guangzhou (CN); Shu Lin, Guangzhou (CN); Jiale Chen, Guangzhou (CN); Runmian Yang, Guangzhou (CN); Huaiyang Fang, Guangzhou (CN); Xiaobao Li, Guangzhou (CN)

(73) Assignee: SOUTH CHINA INSTITUTE OF ENVIRONMENTAL SCIENCE, MEE (ECOLOGICAL AND ENVIRONMENTAL EMERGENCY RESEARCH INSTITUTE, MEE), Guangzhou (CN)

( * ) Notice: Subject to any disclaimer, the term of this patent is extended or adjusted under 35 U.S.C. 154(b) by 372 days.

(21) Appl. No.: 18/181,310

(22) Filed: Mar. 9, 2023

(65) Prior Publication Data

US 2024/0201050 A1 Jun. 20, 2024

(30) Foreign Application Priority Data

Dec. 15, 2022 (CN) .......................... 2022116176234

(51) Int. Cl.
  *G01N 1/12* (2006.01)
  *G01N 15/04* (2006.01)
  *G01N 33/24* (2006.01)

(52) U.S. Cl.
  CPC ............... *G01N 1/12* (2013.01); *G01N 15/04* (2013.01); *G01N 33/246* (2013.01)

(58) Field of Classification Search
  CPC ......... G01N 1/12; G01N 15/04; G01N 33/246
  USPC ....................................................... 73/864.33
  See application file for complete search history.

(56) References Cited

U.S. PATENT DOCUMENTS

| 8,011,239 B1 * | 9/2011 | Chadwick .............. G01N 33/18 210/785 |
| 2021/0208033 A1 * | 7/2021 | Wang ....................... G01N 1/14 |

* cited by examiner

*Primary Examiner* — Peter J Macchiarolo
*Assistant Examiner* — Rodney T Frank
(74) *Attorney, Agent, or Firm* — MUNCY, GEISSLER, OLDS & LOWE, P.C.

(57) ABSTRACT

A device for in-situ measurement of substance migration and transformation on a sediment-water interface includes a floating platform. Three take-up and pay-off components are fixedly connected to the edge of a top surface of the floating platform. Each take-up and pay-off component comprises an L-shaped base, a cable take-up and pay-off assembly, vertical rods, a guide sheave wheel, an adjustment assembly and a first cable. Two DGT samplers are fixedly connected to bottom ends of two three take-up and pay-off components. Water quality monitoring sensors are fixedly connected to the two first cables fixedly connected to the two DGT samplers, respectively. A sediment collector is fixedly connected to a bottom end of the other take-up and pay-off component. Sampling can be performed in-situ directly through DGT flat plates to avoid the impact of environmental changes.

10 Claims, 9 Drawing Sheets

DEVICE FOR IN-SITU MEASUREMENT OF SUBSTANCE MIGRATION AND TRANSFORMATION ON SEDIMENT-WATER INTERFACE

BACKGROUND OF THE INVENTION

1. Technical Field

The invention relates to the technical field of environmental science and engineering, in particular to a device for in-situ measurement of substance migration and transformation on a sediment-water interface.

2. Description of Related Art

With the growth of the global population and the rapid development of the economy, more and more pollutants are discharged into water, leading to water pollution. Exogenous input and endogenous release are two main provenance bases causing the rise of the pollutant concentration. The exogenous input is mainly from the emission of industrial and agricultural production as well as urban life. The endogenous release leads to a water pollution source due to the migration and transformation of corresponding pollutants in sediments and upward release under the action of diffusive gradients in thin-films (DGT), resuspension and bioturbation. At present, with the effective promotion of water ecological environment management, the exogenous input will be effectively controlled eventually, and the endogenous release becomes the main obstacle of water ecological restoration. Existing researches have shown that pollutants released by accumulated sediments in rivers may cause long-term pollution of water even if exogenous pollution is effectively controlled, which indicates the importance of endogenous pollution control. The change of any tiny organisms, chemical reactions and physical environments will have a complex impact on the sediment-water interface where pollutant migration and transformation occur. So, it can provide basic data support for endogenous pollution control to figure out pollutant migration features on the sediment-water interface. DGT, as a technique for in-situ measurement of the ion diffusion flux or the ion concentration in a medium, obtains the concentration of ions by quantitatively measuring and calculating the ions penetrating through a diffusive film with a certain thickness within a specific time based on Fick's first law of diffusion. With the development of DGT, it has been widely used for studying environmental hot issues, including the acquisition of information of metal cations and anions, organic matter and nano-particles, and can be used to study the physical and chemical behaviors and bio-availability of various substances in environmental media in conjunction with an effective mathematic model. At present, the migration and transformation of pollutants on the sediment-water interface are studied typically by collecting surface sediment samples to carry out a simulation experiment or collecting cylindrical samples and then inserting the cylindrical samples in DGT flat plates in a laboratory to capture target particles. However, such a method has the following drawbacks:

This experimental method can measure the diffusion flux and release rate of endogenous pollutants in case of variable water quantity or variable environmental factors. But, it cannot simulate changes caused by the field environment such as wind disturbance or water disturbance and cannot reflect accurate in-situ data of samples, which is not beneficial to research.

In view of this, a device for in-situ measurement of substance migration and transformation on a sediment-water interface is proposed to solve the above-mentioned problems.

BRIEF SUMMARY OF THE INVENTION

The objective of the invention is to provide a device for in-situ measurement of substance migration and transformation on a sediment-water interface to solve the problems mentioned in the description of related Art.

To fulfill the above objective, the invention provides the following technical solution: a device for in-situ measurement of substance migration and transformation on a sediment-water interface comprises a floating platform, wherein three take-up and pay-off components are fixedly connected to an edge of a top surface of the floating platform, each of the take-up and pay-off components comprises an L-shaped base, a cable take-up and pay-off assembly, vertical rods, a guide sheave wheel, an adjustment assembly and a first cable, two DGT samplers are fixedly connected to bottom ends of two of the three take-up and pay-off components, water quality monitoring sensors are fixedly connected to the two first cables fixedly connected to the two DGT samplers, respectively, and a sediment collector is fixedly connected to a bottom end of the other take-up and pay-off component;

The sediment collector comprises a top plate and a bottom plate, four first connecting pillars are vertically and fixedly connected between the top plate and the bottom plate, a sliding hole is vertically formed in the center of the top plate, a fixing rod is vertically and slidably connected into the sliding hole, a counterweight plate is fixedly connected to a bottom end of the fixing rod located below the top plate, two first threaded holes are formed in a bottom surface of the counterweight plate, first studs are threadedly connected into the first threaded holes, two sampling tubes are fixedly connected to bottom ends of the two first studs respectively, two sampling through-holes are vertically formed in the bottom plate and are located at identical vertical positions of the two sampling tubes, and bottom ends of the sampling tubes are open;

Each of the DGT samplers comprises a top circular plate and a bottom circular plate, four second connecting pillars are fixedly connected between the top circular plate and the bottom circular plate, two second threaded holes are formed in top surfaces of two sides of the bottom circular plate respectively, two second studs are threadedly connected into the two second threaded holes respectively, and two DGT flat plates are fixedly connected to top ends of the two second studs respectively.

Preferably, a square frame is fixedly connected to a top surface of the bottom plate and is located on an outer side of the two sampling through-holes, two sealing plates are slidably connected two inner sides of the square frame respectively, a top end of the fixing rod is fixedly connected to a bottom end of the first cable, and a stop plate is horizontally and fixedly connected to the fixing rod located above the top plate.

Preferably, two sliding grooves are formed in an inner wall of the square frame, two sliding blocks are slidably connected into the two sliding grooves respectively, the two sliding blocks are fixedly connected to the two sealing plates respectively, a double-shaft gear motor is fixedly connected into the square frame and is located between the two sliding grooves, two shaft levers are fixedly connected to two shaft ends of the double-shaft gear motor, two first lead screws are rotatably connected into the two sliding grooves respectively, first threaded sleeves are fixedly connected into the sliding blocks, the first lead screws are threadedly connected to the first threaded sleeves, ends of the two shaft levers are fixedly connected to ends of the two first lead screws respectively, and threads on the two first lead screws are in opposite directions.

Preferably, a bottom opening is formed in the bottom circular plate and is located between the two DGT flat plates, multiple cross-bars are horizontally and fixedly connected into the bottom opening, multiple vertical counterweight plates are vertically and fixedly connected to the multiple cross-bars respectively, a connecting post is fixedly connected to the center of a top surface of the top circular plate, and a top end of the connecting post is fixedly connected to the first cable.

Preferably, a power distribution box and a central control unit are fixedly connected to the top surface of the floating platform, a second cable is vertically and fixedly connected to the center of a bottom surface of the floating platform, a balancing weight is fixedly connected to a bottom end of the second cable, the central control unit comprises a shell fixedly connected to the top surface of the floating platform, a touch display screen is fixedly connected to one side of a top surface of the shell, a host computer and a transmission module are fixedly connected into the shell, and a wiring board and a control panel are fixedly connected to a side wall of the shell.

Preferably, four fences are vertically and fixedly connected to the edge of the top surface of the floating platform, three oblique support frames are fixedly connected to the top surface of the floating platform and are located around the power distribution box, three photovoltaic panels are fixedly connected to the three oblique support frames respectively, and an automatic meteorological station is fixedly connected to the top surface of the floating platform.

Preferably, the L-shaped base is fixedly connected to an edge of the floating platform, the cable take-up and pay-off assembly is fixedly connected to an end of a top surface of the L-shaped base, the adjustment assembly is horizontally and fixedly connected to a side, away from the cable take-up and pay-off assembly, of the L-shaped base, the cable take-up and pay-off assembly comprises two vertical plates fixedly connected to the top surface of the L-shaped base, a reel is rotatably connected between top ends of the two vertical plates, a motor support is fixedly connected to the top surface of the L-shaped base, a first gear motor is fixedly connected to the motor support, a shaft end of the first gear motor is fixedly connected to a shaft end of the reel, the first cable is wound on the reel, and an end of the first cable is fixedly connected to the reel.

Preferably, the two vertical rods are vertically and fixedly connected to the top surface of the L-shaped base and are located between the cable take-up and pay-off assembly and the adjustment assembly, a guide sheave wheel is rotatably connected between top ends of the two vertical rods, and the first cable is in contact with a top surface of the guide sheave wheel.

Preferably, the adjustment assembly comprises a bracket fixedly connected to a side wall of the L-shaped base, a horizontal rod is horizontally and rotatably connected to an end, away from the L-shaped base, of the bracket, a sliding notch is formed in an end, away from the bracket, of the horizontal rod, a sliding column is horizontally and slidably connected into the sliding notch, an adjustment plate is fixedly connected to an end, away from the horizontal rod, of the sliding column, two adjustment sheave wheels are rotatably connected to the adjustment plate, and the first cable passes between the two adjustment sheave wheels.

Preferably, two shaft columns are fixedly connected to a top surface and a bottom surface of an end of the horizontal rod respectively, the shaft columns are rotatably connected to a side wall of the bracket, a motor shell is fixedly connected to a bottom surface of the bracket, a second gear motor is fixedly connected into the motor shell, a shaft end of the second gear motor is fixedly connected to an end of one of the two shaft columns, a third gear motor is fixedly connected into the horizontal rod and is located at a position close to the bracket, a second lead screw is horizontally and rotatably connected into the sliding notch, a cavity is formed in an end, close to the horizontal rod, of the sliding column, a second threaded sleeve is fixedly connected to an end of the cavity, the second lead screw is threadedly connected to the second threaded sleeve, and an end of the second lead screw is located in the cavity.

Compared with the prior art, the invention has the following beneficial effects:

In the invention, sampling can be performed in-situ directly through the DGT flat plates to avoid the impact of environmental changes, such that data is more accurate and can more truly reflect the condition of the samples in the actual environment; and in-situ observation, and collection and analysis of cylindrical samples can be performed at the same time, and the pollutant migration and transformation mechanism can be better studied according to these two types of data.

Figure 1:
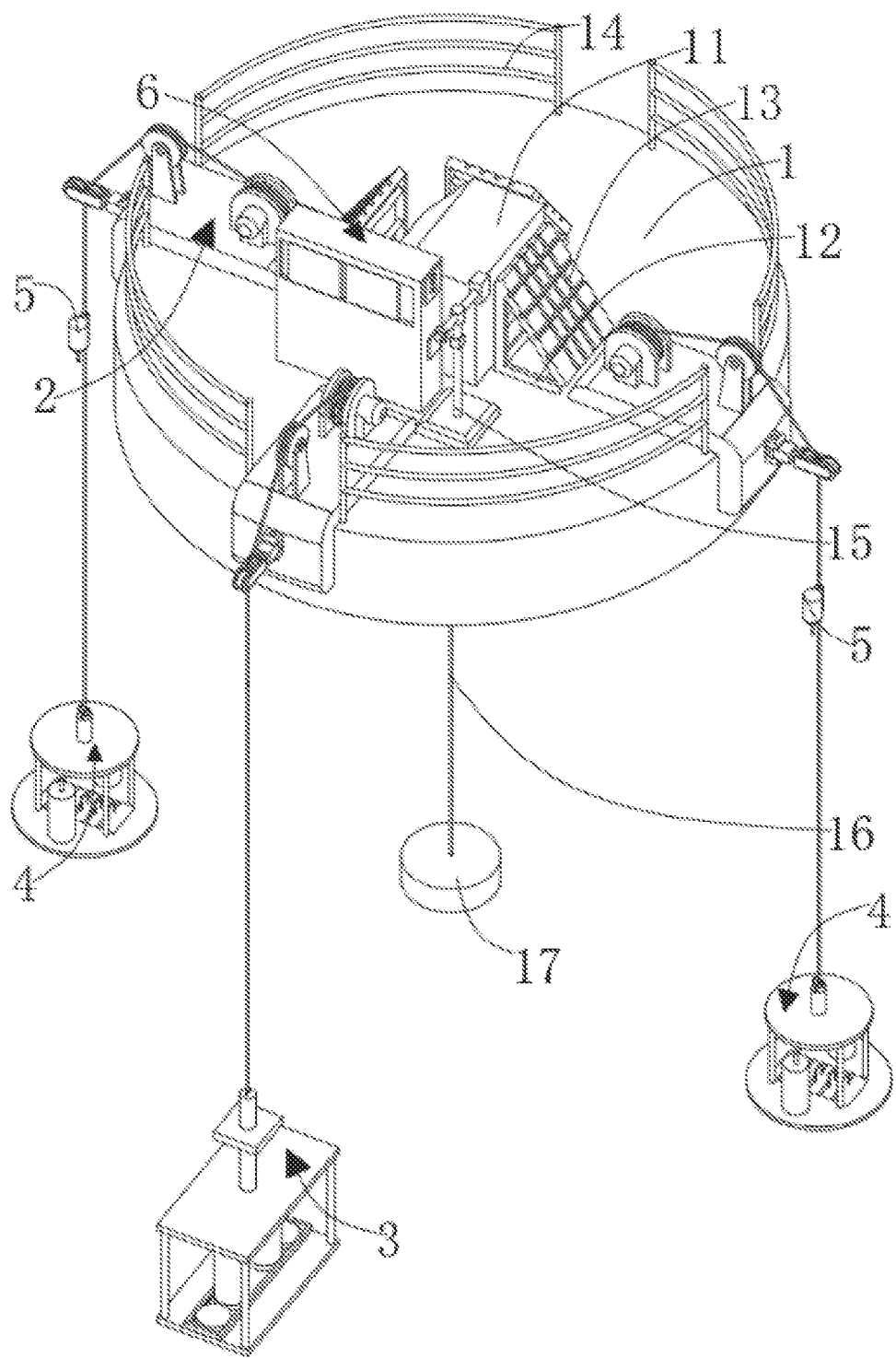
FIG. 1 is a structural view of a main part in Embodiment 1 and Embodiment 2 of the invention.
Figure 2:
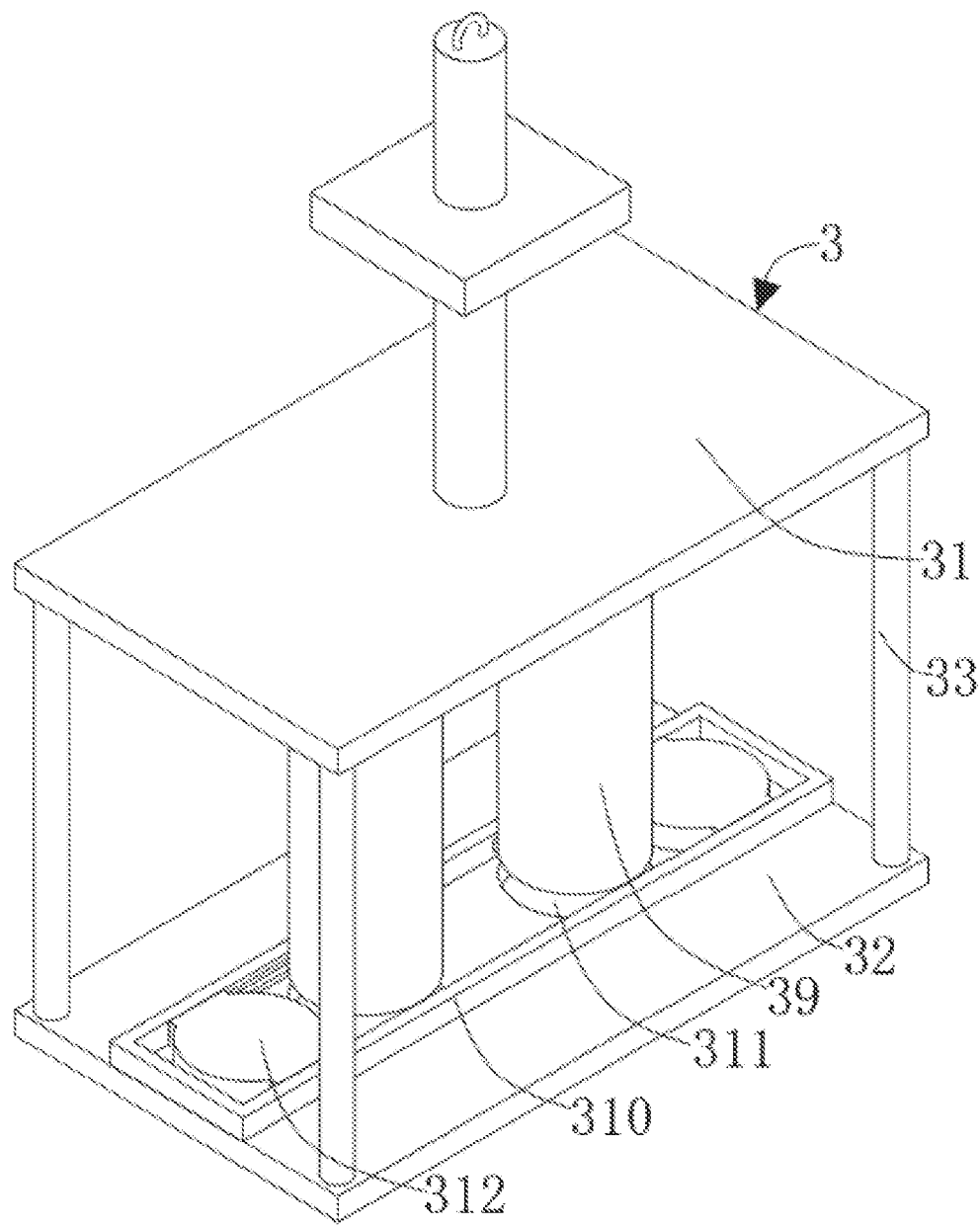
FIG. 2 is a structural view of a sediment collector in Embodiment 1 and Embodiment 2 of the invention.
Figure 3:
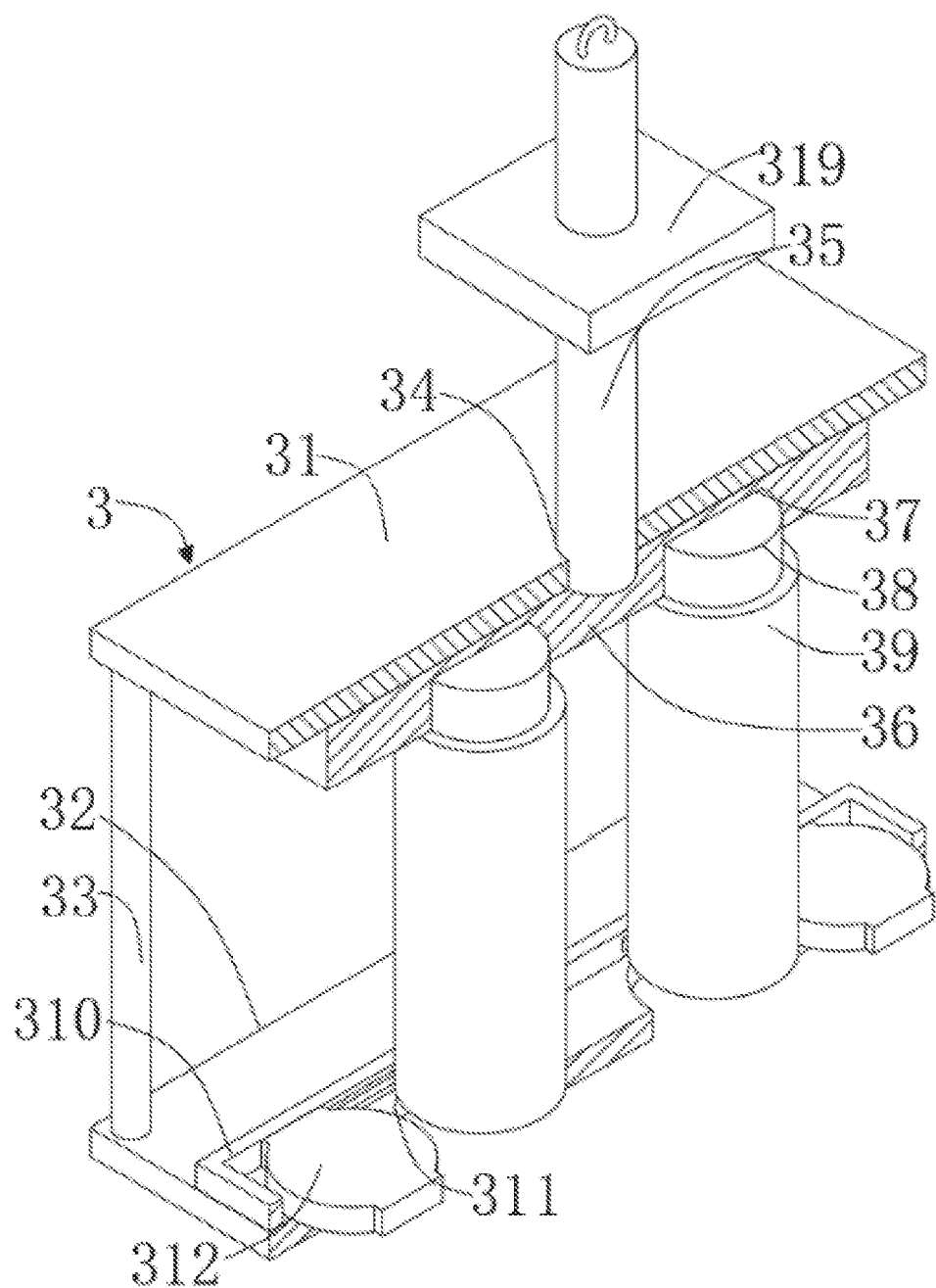
FIG. 3 is a sectional structural view of the sediment collector in Embodiment 1 and Embodiment 2 of the invention.
Figure 4:
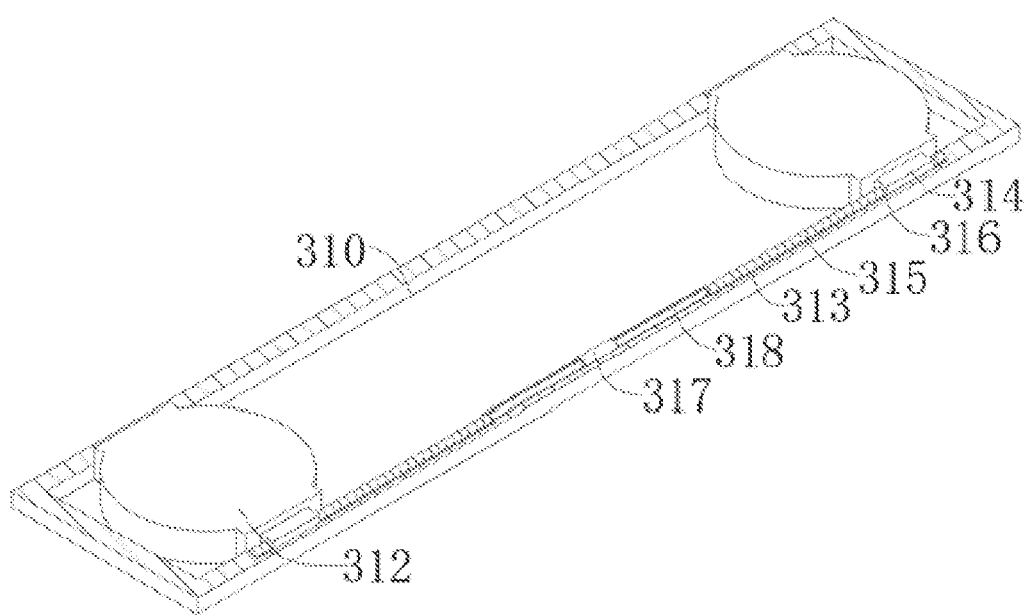
FIG. 4 is a sectional structural view of a square frame in Embodiment 2 of the invention.
Figure 5:
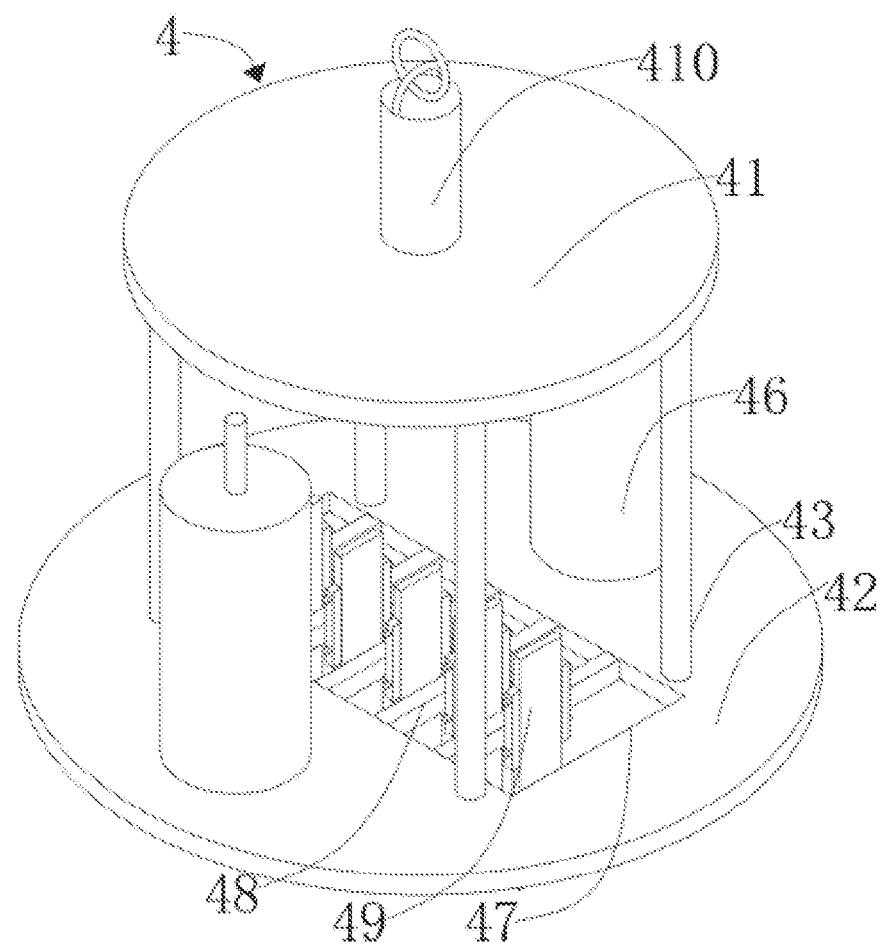
FIG. 5 is a structural view of a DGT sampler in Embodiment 1 and Embodiment 2 of the invention.
Figure 6:
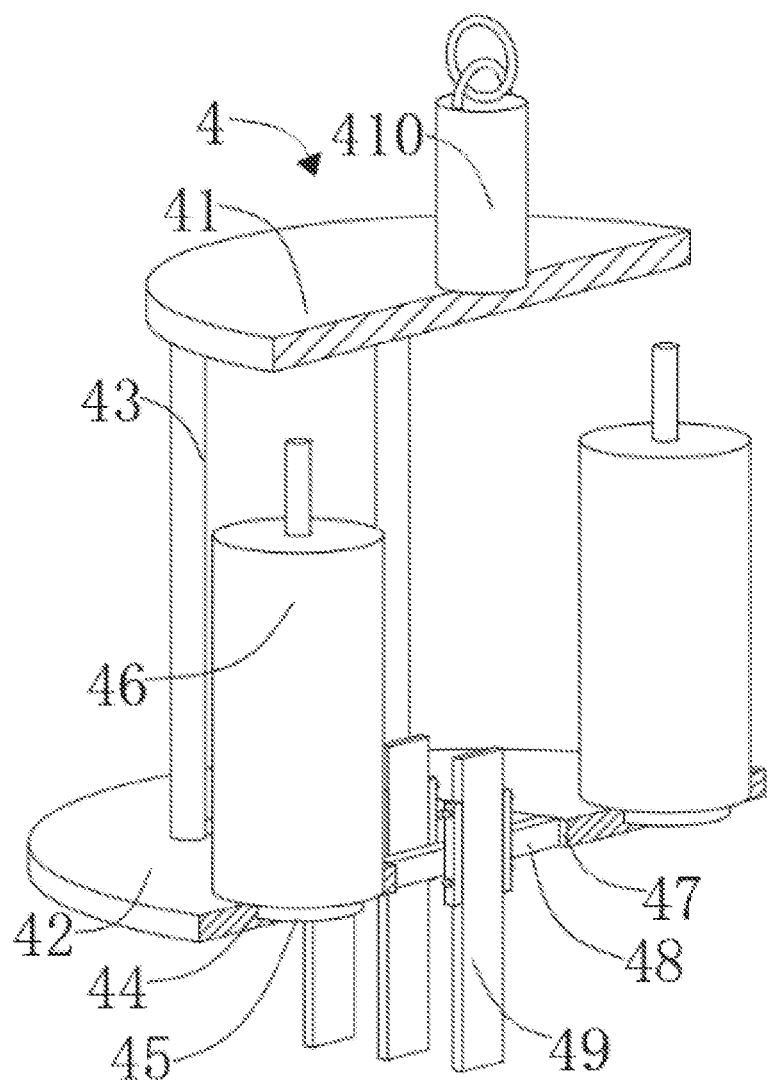
FIG. 6 is a sectional structural view of the DGT sampler in Embodiment 1 and Embodiment 2 of the invention.

In the figures: 1, floating platform; 2, take-up and pay-off component; 3, sediment collector; 4, DGT sampler; 5, water quality monitoring sensor; 6, central control unit; 11, power distribution box; 12, oblique support frame; 13, photovoltaic panel; 14, fence; 15, automatic meteorological station; 16, second cable; 17, balancing weight; 21, L-shaped base; 22, cable take-up and pay-off assembly; 23, vertical rod; 24, guide sheave wheel; 25, adjustment assembly; 26, first cable; 221, vertical plate; 222, reel; 223, first gear motor; 224, motor support; 251, bracket; 252, horizontal rod; 253, sliding notch; 254, sliding column; 255, adjustment plate; 256, adjustment sheave wheel; 257, shaft column; 258, motor shell; 259, second gear motor; 2510, third gear motor; 2511, second lead screw; 2512, second threaded sleeve; 2513, cavity; 31, top plate; 32, bottom plate; 33, first connecting pillar; 34, sliding hole; 35, fixing rod; 36, counterweight plate; 37, first threaded hole; 38, first stud; 39, sampling tube; 310, square frame; 311, sampling through-hole; 312, sealing plate; 313, sliding groove; 314, sliding block; 315, first lead screw; 316, first threaded sleeve; 317, double-shaft gear motor; 318, shaft lever; 319, stop plate; 41, top circular plate; 42, bottom circular plate; 43, second connecting pillar; 44, second threaded hole; 45, second stud; 46, DGT flat plate; 47, bottom opening; 48, cross-bar; 49, vertical counterweight plate; 410, connecting post; 61, shell; 62, touch display screen; 63, host computer; 64, transmission module; 65, wiring board; 66, control panel.

DETAILED DESCRIPTION OF THE INVENTION

The technical solutions of the embodiments of the invention will be clearly and completely described below in conjunction with the accompanying drawings of the embodiments of the invention. Obviously, the following embodiments are merely illustrative ones, and are not all possible ones of the invention. All other embodiments obtained by those ordinarily skilled in the art based on the following ones without creative labor should also fall within the protection scope of the invention.

Embodiment 1

Referring to FIG. 1-FIG. 3 and FIG. 5-FIG. 6, the invention provides the following technical solution: a device for in-situ measurement of substance migration and transformation on a sediment-water interface comprises a floating platform 1, wherein three take-up and pay-off components 2 are fixedly connected to the edge of a top surface of the floating platform 1, each take-up and pay-off component 2 comprises an L-shaped base 21, a cable take-up and pay-off assembly 22, vertical rods 23, a guide sheave wheel 24, an adjustment assembly 25 and a first cable 26, two DGT samplers 4 are fixedly connected to bottom ends of two take-up and pay-off components 2, water quality monitoring sensors 5 are fixedly connected to the two first cables 26 fixedly connected to the two DGT samplers 4, respectively, and a sediment collector 3 is fixedly connected to a bottom end of the other take-up and pay-off component 2;

The sediment collector 3 comprises a top plate 31 and a bottom plate 32, wherein four first connecting pillars 33 are vertically and fixedly connected between the top plate 31 and the bottom plate 32, a sliding hole 34 is vertically formed in the center of the top plate 31, a fixing rod 35 is vertically and slidably connected into the sliding hole 34, a counterweight plate 36 is fixedly connected to a bottom end of the fixing rod 35 located below the top plate 31, two first threaded holes 37 are formed in a bottom surface of the counterweight plate 36, first studs 38 are threadedly connected into the first threaded holes 37, two sampling tubes 39 are fixedly connected to bottom ends of the two first studs 38, respectively, two sampling through-holes 311 are vertically formed in the bottom plate 32 and are located at identical vertical positions of the two sampling tubes 39, and bottom ends of the sampling tubes 39 are open; when the sediment collector 3 is used for collecting sediments, the first cable 26 is laid down through the take-up and pay-off component 2, the bottom plate 32 of the sediment collector 3 reaches the bottom at first, then the first cable 26 is further laid down, the two sampling tubes 39 descend stably and slowly under the action of the gravity of the counterweight plate 36 to be pressed into the sediments and are kept static for 5-10 minutes, and when the sampling tubes 39 are completely inserted into the sediments, samples enter the sampling tubes 39; then, the first cable 26 is pulled upwards, the sampling tubes 39 rise synchronously, at this moment, bottoms of the sampling tubes 39 are sealed by sealing plates 312, and the first cable 26 is further pulled upwards to retrieve the sediment collector 3;

Each DGT sampler 4 comprises a top circular plate 41 and a bottom circular plate 42, four second connecting pillars 43 are fixedly connected between the top circular plate 41 and the bottom circular plate 42, two second threaded holes 44 are formed in top surfaces of two sides of the bottom circular plate 42 respectively, two second studs 45 are threadedly connected into the two second threaded holes 44 respectively, and two DGT flat plates 46 are fixedly connected to top ends of the two second studs 45 respectively; and when the DGT sampler 4 is used for sampling, the first cable 26 is laid down, the bottom circular plate 42 is placed on a sediment-water interface by means of vertical counterweight plates 49, and bottom ends of the vertical counterweight plates 49 are inserted into the sediments until they reach the bottom, wherein the number of the DGT flat plates 46 can be increased according to the types of collected pollutants; and the DGT sampler 4 is retrieved 24 hours later, and the DGT flat plates 46 are detached from the DGT sampler 4.

Embodiment 2

Refer to FIG. 1-6 and FIG. 9 which illustrate Embodiment 2 of the invention. In Embodiment 2 which is based on Embodiment 1, a square frame 310 is fixedly connected to a top surface of the bottom plate 32 and is located on an outer side of the two sampling through-holes 311, two sealing plates 312 are slidably connected to two inner sides of the square frame 310 respectively, a top end of the fixing rod 35 is fixedly connected to a bottom end of the first cable 26, and a stop plate 319 is horizontally and fixedly connected to the fixing rod 35 located above the top plate 31.

Two sliding grooves 313 are formed in an inner wall of the square frame 310, two sliding blocks 314 are slidably connected into the two sliding grooves 313 and are fixedly connected to the two sealing plates 312 respectively, a double-shaft gear motor 317 is fixedly connected into the square frame 310 and is located between the two sliding grooves 313, two shaft levers 318 are fixedly connected to two shaft ends of the double-shaft gear motor 317 respectively, two first lead screws 315 are rotatably connected into the two sliding grooves 313 respectively, first threaded sleeves 316 are fixedly connected into the sliding blocks 314, the first lead screws 315 are threadedly connected to the first threaded sleeves 316, ends of the two shaft levers 318 are fixedly connected to ends of the two first lead screws 315 respectively, threads on the two first lead screws 315 are in opposite directions, the double-shaft gear motor 317 drives the two first lead screws 315 to rotate, so as to drive the two sealing plates 312 to move through the first threaded sleeves 316, and after sampling is finished, the bottoms of the sampling tubes 39 are sealed by the sealing plates 312.

A bottom opening 47 is formed in the bottom circular plate 42 and is located between the two DGT flat plates 46, multiple cross-bars 48 are horizontally and fixedly connected into the bottom opening 47, multiple vertical counterweight plates 49 are vertically and fixedly connected to the multiple cross-bars 48 respectively, a connecting post 410 is fixedly connected to the center of a top surface of the top circular plate 41, and a top end of the connecting post 410 is fixedly connected to the first cable 26.

A power distribution box 11 and a central control unit 6 are fixedly connected to the top surface of the floating platform 1, a second cable 16 is vertically and fixedly connected to the center of a bottom surface of the floating platform 1, a balancing weight 17 is fixedly connected to a bottom end of the second cable 16, the central control unit 6 comprises a shell 61 fixedly connected to the top surface of the floating platform 1, a touch display screen 62 is fixedly connected to one side of a top surface of the shell 61, a host computer 63 and a transmission module 64 are fixedly connected into the shell 61, a wiring board 65 and a control panel 66 are fixedly connected to a side wall of the shell 61, and the control panel 66 is used for controlling the take-up and pay-off components 2 and the double-shaft gear motor 317 in the sediment collector 3.

Four fences 14 are vertically and fixedly connected to the edge of the top surface of the floating platform 1, three oblique support frames 12 are fixedly connected to the top surface of the floating platform 1 and are located around the power distribution box 11, three photovoltaic panels 13 are fixedly connected to the three oblique support frames 12 respectively, and an automatic meteorological station 15 is fixedly connected to the top surface of the floating platform 1 and is used for recording meteorological data such as wind speed, wind direction, air temperature, air humidity, air pressure, and rainfall.

Embodiment 3

Figure 7:
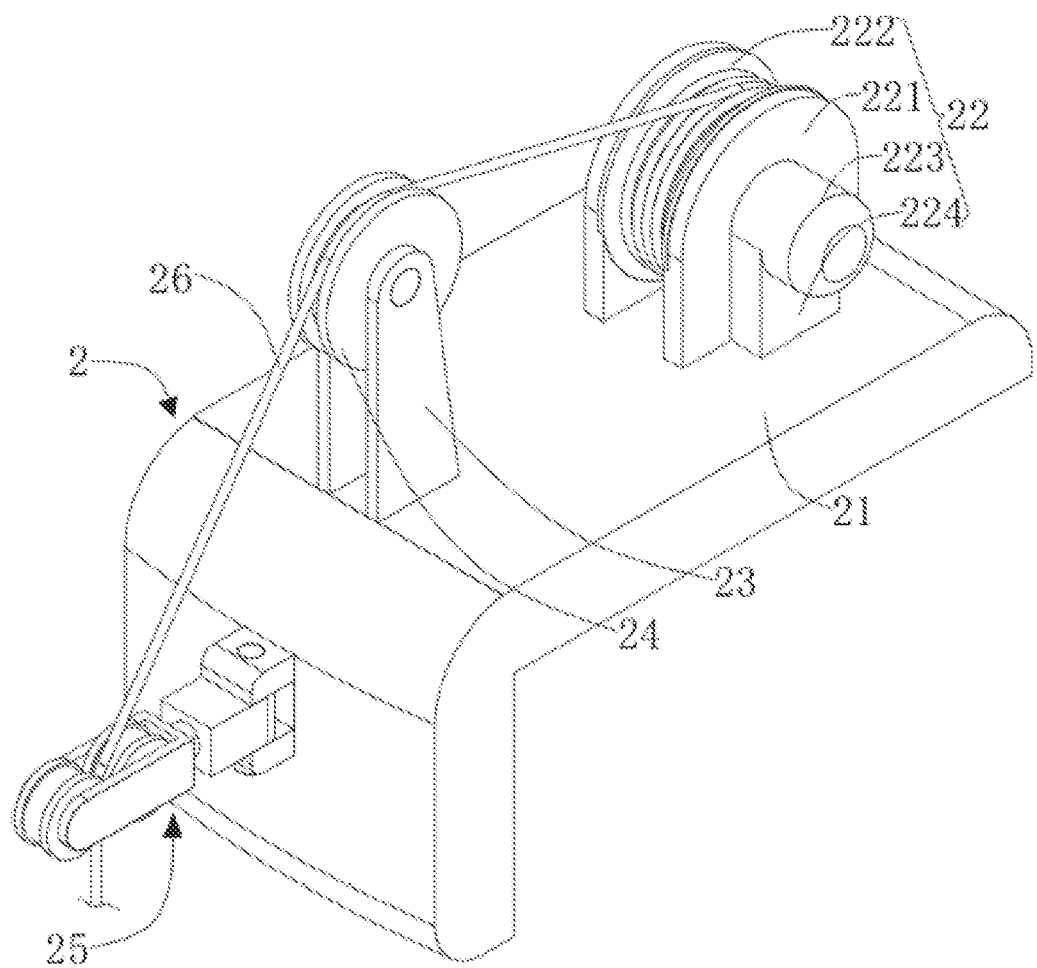
FIG. 7 is a structural view of a take-up and pay-off component in Embodiment 3 of the invention.
Figure 8:
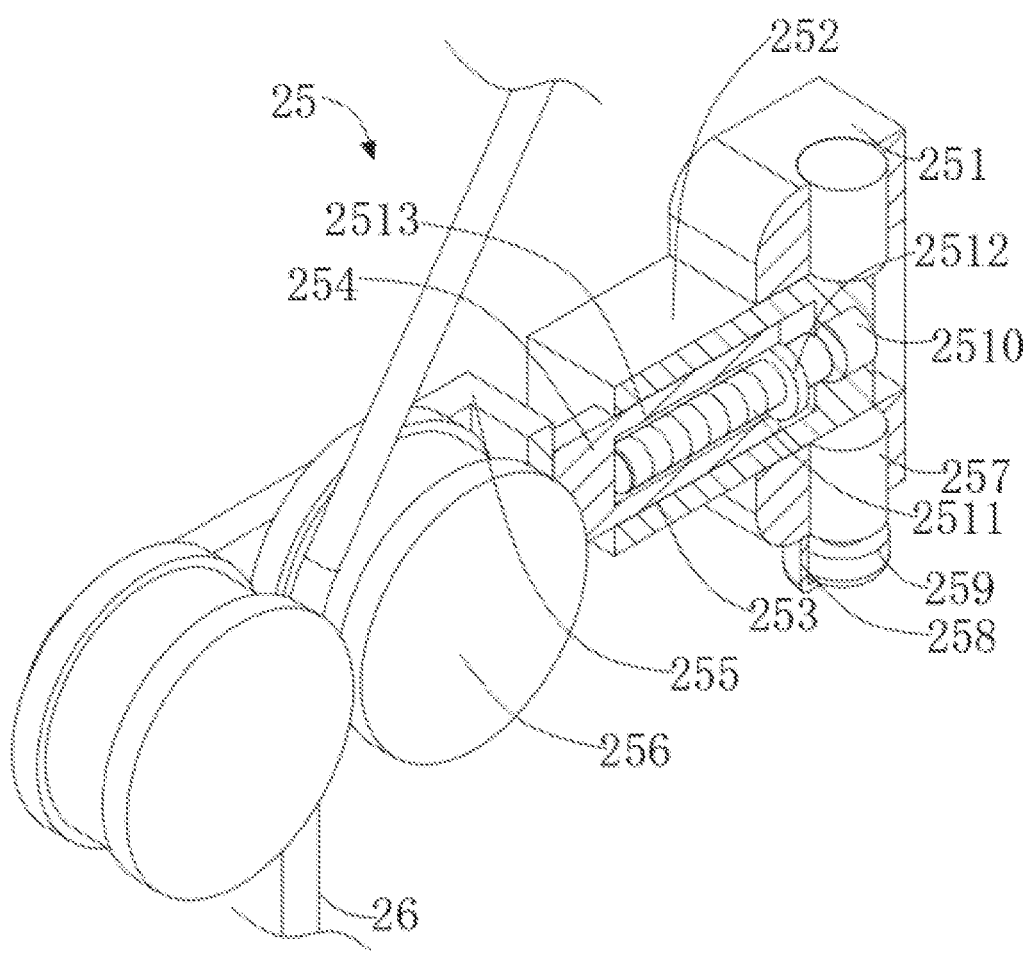
FIG. 8 is a sectional structural view of an adjustment assembly in Embodiment 3 of the invention.
Figure 9:
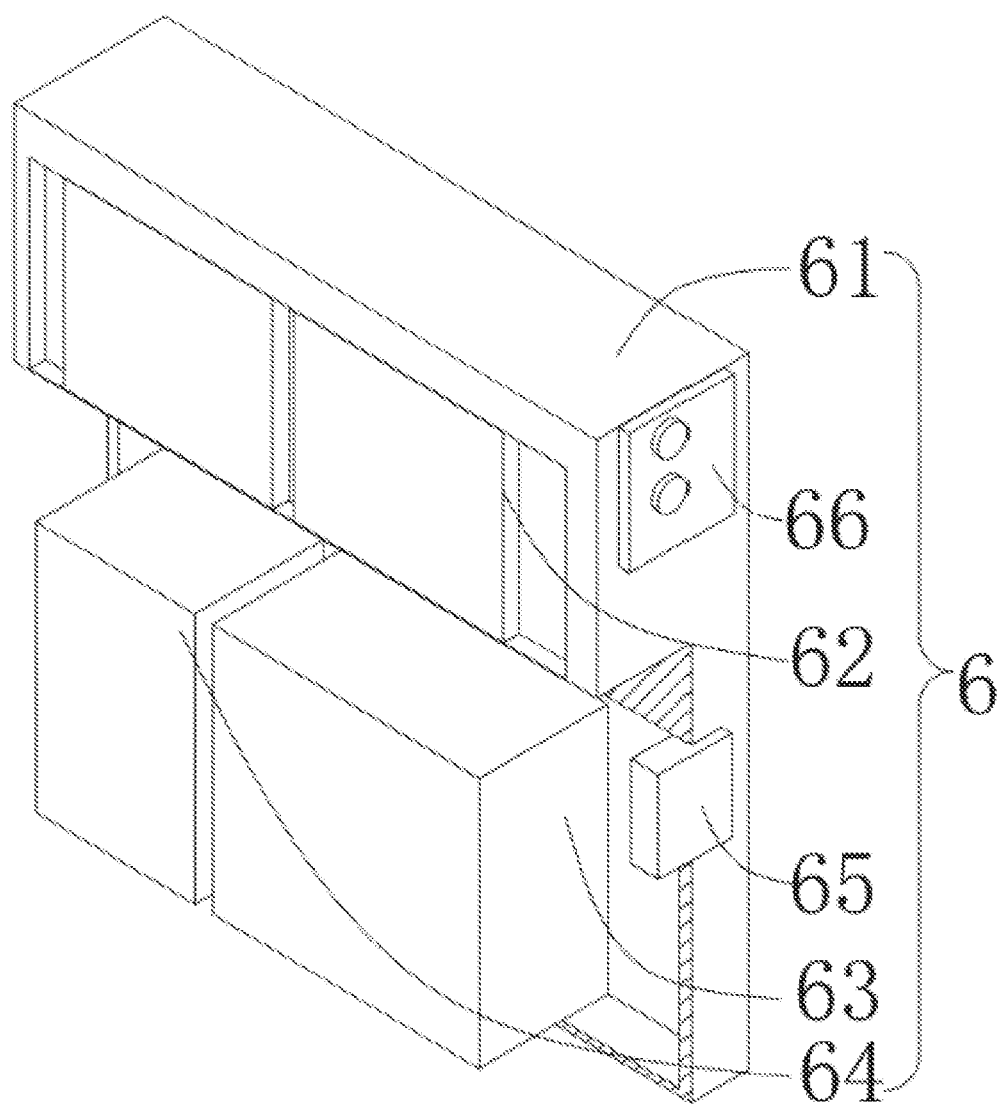
FIG. 9 is a sectional structural view of a central control unit in Embodiment 2 of the invention.

Refer to FIG. 7-FIG. 8 which illustrate Embodiment 3 of the invention. In Embodiment 3 which is based on the above two embodiments, the L-shaped base 21 is fixedly connected to the edge of the floating platform 1, the cable take-up and pay-off assembly 22 is fixedly connected to the end of a top surface of the L-shaped base 21, the adjustment assembly 25 is horizontally and fixedly connected to a side, away from the cable take-up and pay-off assembly 22, of the L-shaped base 21, the cable take-up and pay-off assembly 22 comprises two vertical plates 221 fixedly connected to the top surface of the L-shaped base 21, a reel 222 is rotatably connected between top ends of the two vertical plates 221, a motor support 224 is fixedly connected to the top surface of the L-shaped base 21, a first gear motor 223 is fixedly connected to the motor support 224, a shaft end of the first gear motor 223 is fixedly connected to a shaft end of the reel 222, the first cable 26 is wound on the reel 222, and the end of the first cable 26 is fixedly connected to the reel 222.

Two vertical rods 23 are vertically and fixedly connected to the top surface of the L-shaped base 21 and are located between the cable take-up and pay-off assembly 22 and the adjustment assembly 25, the guide sheave wheel 24 is rotatably connected between top ends of the two vertical rods 23, and the first cable 26 is in contact with a top surface of the guide sheave wheel 24.

The adjustment assembly 25 comprises a bracket 251 fixedly connected to a side wall of the L-shaped base 21, a horizontal rod 252 is horizontally and rotatably connected to an end, away from the L-shaped base 21, of the bracket 251, a sliding notch 253 is formed in an end, away from the bracket 251, of the horizontal rod 252, a sliding column 254 is horizontally and slidably connected into the sliding notch 253, an adjustment plate 255 is fixedly connected to an end, away from the horizontal rod 252, of the sliding column 254, two adjustment sheave wheels 256 are rotatably connected to the adjustment plate 255, and the first cable 26 passes between the two adjustment sheave wheels 256.

Two shaft columns 257 are fixedly connected to a top surface and a bottom surface of an end of the horizontal rod 252 respectively and are rotatably connected to a side wall of the bracket 251, a motor shell 258 is fixedly connected to a bottom surface of the bracket 251, a second gear motor 259 is fixedly connected into the motor shell 258, a shaft end of the second gear motor 259 is fixedly connected to the end of one shaft column 257, a third gear motor 2510 is fixedly connected into the horizontal rod 252 and is located at a position close to the bracket 251, a second lead screw 2511 is horizontally and rotatably connected into the sliding notch 253, a cavity 2513 is formed in an end, close to the horizontal rod 252, of the sliding column 254, a second threaded sleeve 2512 is fixedly connected to an end of the cavity 2513, a second lead screw 2511 is threadedly connected to the second threaded sleeve 2512, an end of the second lead screw 2511 is located in the cavity 2513, the second gear motor 259 drives the adjustment plate 255 to swing horizontally, and the third gear motor 2510 drives the sliding column 254 to slide to change the horizontal length of the adjustment plate 255, such that the position where the first cable 26 is laid can be slightly adjusted to perform sampling at a designated position more accurately.

Embodiment 4

When the device is used for collecting sediments, the first cable 26 is laid down through the take-up and pay-off component 2, the bottom plate 32 of the sediment collector 3 reaches the bottom first, then the first cable 26 is further laid down, the two sampling tubes 39 descend stably and slowly under the action of the gravity of the counterweight plate 36 to be pressed into the sediments and are kept static for 5-10 minutes, and when the sampling tubes 39 are completely inserted into the sediments, samples enter the sampling tubes 39; then, the first cable 26 is pulled upwards, the sampling tubes 39 rise synchronously, at this moment, the bottoms of the sampling tubes 39 are sealed by the sealing plates 312, the first cable 26 is further pulled upwards to retrieve the sediment collector 3, and the sampling tubes 39 are detached from the sediment collector to obtain the samples. When the DGT flat plates 46 are used for collection, the first cable 26 is laid down, the bottom circular plate 42 is placed on a sediment-water interface by means of the vertical counterweight plates 49, and the bottom ends of the vertical counterweight plates 49 are inserted into the sediments until they reach the bottom, wherein the number of the DGT flat plates 46 can be increased according to the types of collected pollutants; and the DGT sampler 4 is retrieved 24 hours later, and the DGT flat plates 46 are detached from the DGT sampler 4. In the invention, sampling can be performed in-situ directly through the DGT flat plates 46 to avoid the impact of environmental changes, such that data is more accurate and can more truly reflect the condition of the samples in the actual environment; and in-situ observation, and collection and analysis of cylindrical samples can be performed at the same time, and the pollutant migration and transformation mechanism can be better studied according to these two types of data.

Although the embodiments of the invention have been illustrated and described above, those ordinarily skilled in the art should understand that various changes, amendments, substitutions and transformations can be made without departing from the principle and spirit of the invention. The scope of the invention should be defined by the claims and their equivalents.

What is claimed is:

1. A device for in-situ measurement of substance migration and transformation on a sediment-water interface, comprising: a floating platform, wherein: three take-up and pay-off components are fixedly connected to an edge of a top surface of the floating platform, each of the take-up and pay-off components comprises an L-shaped base, a cable take-up and pay-off assembly, vertical rods, a guide sheave wheel, an adjustment assembly and a first cable, two Diffusive Gradients in Thin-Films (DGT) samplers are fixedly connected to bottom ends of two of the three take-up and pay-off components, water quality monitoring sensors are fixedly connected to the two first cables fixedly connected to the two DGT samplers, respectively, and a sediment collector is fixedly connected to a bottom end of the other take-up and pay-off component; the sediment collector comprises a top plate and a bottom plate, four first connecting pillars are vertically and fixedly connected between the top plate and the bottom plate, a sliding hole is vertically formed in a center of the top plate, a fixing rod is vertically and slidably connected into the sliding hole, a counterweight plate is fixedly connected to a bottom end of the fixing rod located below the top plate, two first threaded holes are formed in a bottom surface of the counterweight plate, first studs are threadedly connected into the first threaded holes, two sampling tubes are fixedly connected to bottom ends of the two first studs respectively, two sampling through-holes are vertically formed in the bottom plate and are located at identical vertical positions of the two sampling tubes, and bottom ends of the sampling tubes are open, each of the DGT samplers comprises a top circular plate and a bottom circular plate, four second connecting pillars are fixedly connected between the top circular plate and the bottom circular plate, two second threaded holes are formed in top surfaces of two sides of the bottom circular plate respectively, two second studs are threadedly connected into the two second threaded holes respectively, and two DGT flat plates are fixedly connected to top ends of the two second studs respectively.

2. The device for in-situ measurement of substance migration and transformation on a sediment-water interface according to claim 1, wherein a square frame is fixedly connected to a top surface of the bottom plate and is located on an outer side of the two sampling through-holes, two sealing plates are slidably connected two inner sides of the square frame respectively, a top end of the fixing rod is fixedly connected to a bottom end of the first cable, and a stop plate is horizontally and fixedly connected to the fixing rod located above the top plate.

3. The device for in-situ measurement of substance migration and transformation on a sediment-water interface according to claim 2, wherein two sliding grooves are formed in an inner wall of the square frame, two sliding blocks are slidably connected into the two sliding grooves respectively, the two sliding blocks are fixedly connected to the two sealing plates respectively, a double-shaft gear motor is fixedly connected into the square frame and is located between the two sliding grooves, two shaft levers are fixedly connected to two shaft ends of the double-shaft gear motor, two first lead screws are rotatably connected into the two sliding grooves respectively, first threaded sleeves are fixedly connected into the sliding blocks, the first lead screws are threadedly connected to the first threaded sleeves, ends of the two shaft levers are fixedly connected to ends of the two first lead screws respectively, and threads on the two first lead screws are in opposite directions.

4. The device for in-situ measurement of substance migration and transformation on a sediment-water interface according to claim 1, wherein a bottom opening is formed in the bottom circular plate and is located between the two DGT flat plates, multiple cross-bars are horizontally and fixedly connected into the bottom opening, multiple vertical counterweight plates are vertically and fixedly connected to the multiple cross-bars respectively, a connecting post is fixedly connected to a center of a top surface of the top circular plate, and a top end of the connecting post is fixedly connected to the first cable.

5. The device for in-situ measurement of substance migration and transformation on a sediment-water interface according to claim 1, wherein a power distribution box and a central control unit are fixedly connected to the top surface of the floating platform, a second cable is vertically and fixedly connected to a center of a bottom surface of the floating platform, a balancing weight is fixedly connected to a bottom end of the second cable, the central control unit comprises a shell fixedly connected to the top surface of the floating platform, a touch display screen is fixedly connected to one side of a top surface of the shell, a host computer and a transmission module are fixedly connected into the shell, and a wiring board and a control panel are fixedly connected to a side wall of the shell.

6. The device for in-situ measurement of substance migration and transformation on a sediment-water interface according to claim 5, wherein four fences are vertically and fixedly connected to the edge of the top surface of the floating platform, three oblique support frames are fixedly connected to the top surface of the floating platform (1) and are located around the power distribution box, three photovoltaic panels are fixedly connected to the three oblique support frames respectively, and an automatic meteorological station is fixedly connected to the top surface of the floating platform.

7. The device for in-situ measurement of substance migration and transformation on a sediment-water interface according to claim 1, wherein the L-shaped base is fixedly connected to an edge of the floating platform, the cable take-up and pay-off assembly is fixedly connected to an end of a top surface of the L-shaped base, the adjustment assembly is horizontally and fixedly connected to a side, away from the cable take-up and pay-off assembly, of the L-shaped base, the cable take-up and pay-off assembly comprises two vertical plates fixedly connected to the top surface of the L-shaped base, a reel is rotatably connected between top ends of the two vertical plates, a motor support is fixedly connected to the top surface of the L-shaped base, a first gear motor is fixedly connected to the motor support, a shaft end of the first gear motor is fixedly connected to a shaft end of the reel, the first cable is wound on the reel, and an end of the first cable is fixedly connected to the reel.

8. The device for in-situ measurement of substance migration and transformation on a sediment-water interface according to claim 7, wherein the two vertical rods are vertically and fixedly connected to the top surface of the L-shaped base and are located between the cable take-up and pay-off assembly and the adjustment assembly, a guide sheave wheel is rotatably connected between top ends of the two vertical rods, and the first cable is in contact with a top surface of the guide sheave wheel.

9. The device for in-situ measurement of substance migration and transformation on a sediment-water interface according to claim 7, wherein the adjustment assembly comprises a bracket fixedly connected to a side wall of the L-shaped base, a horizontal rod is horizontally and rotatably connected to an end, away from the L-shaped base, of the bracket, a sliding notch is formed in an end, away from the bracket, of the horizontal rod, a sliding column is horizontally and slidably connected into the sliding notch, an adjustment plate is fixedly connected to an end, away from the horizontal rod, of the sliding column, two adjustment sheave wheels are rotatably connected to the adjustment plate, and the first cable passes between the two adjustment sheave wheels.

10. The device for in-situ measurement of substance migration and transformation on a sediment-water interface according to claim 9, wherein two shaft columns are fixedly connected to a top surface and a bottom surface of an end of the horizontal rod respectively, the shaft columns are rotatably connected to a side wall of the bracket (251), a motor shell is fixedly connected to a bottom surface of the bracket, a second gear motor is fixedly connected into the motor shell, a shaft end of the second gear motor is fixedly connected to an end of one of the two shaft columns, a third gear motor is fixedly connected into the horizontal rod and is located at a position close to the bracket, a second lead screw is horizontally and rotatably connected into the sliding notch, a cavity (is formed in an end, close to the horizontal rod, of the sliding column, a second threaded sleeve is fixedly connected to an end of the cavity, the second lead screw is threadedly connected to the second threaded sleeve, and an end of the second lead screw is located in the cavity.

\* \* \* \* \*